United States Patent [19]

Kotraba et al.

[11] Patent Number: 5,894,096
[45] Date of Patent: Apr. 13, 1999

[54] THROUGH-THE-DECK BLAST-HOLE SAMPLER

[75] Inventors: Michael R. Kotraba; Michael Kennedy, both of Fallon; Jerry Minor, Hawthorne; Keith Tom, Schurz, all of Nev.

[73] Assignee: Kennecott Rawhide Mining Company, Fallon, Nev.

[21] Appl. No.: 08/921,043

[22] Filed: Aug. 29, 1997

[51] Int. Cl.⁶ ...................................................... G01N 1/12
[52] U.S. Cl. ............................................ 73/864.63; 15/257.6
[58] Field of Search ............ 73/863.41, 863.51–863.57, 73/863.61, 864.51, 864.63, 864.67; 15/257.1–257.9

[56] References Cited

U.S. PATENT DOCUMENTS

| | | | |
|---|---|---|---|
| 958,590 | 5/1910 | Perry . | |
| 1,471,015 | 10/1923 | Tomkins . | |
| 1,480,562 | 1/1924 | Mock | 15/257.6 |
| 2,171,187 | 8/1939 | Millner | 15/257.5 |
| 3,005,347 | 10/1961 | Smithson | 73/863.55 |
| 3,122,019 | 2/1964 | Wellenius et al. | 73/863.55 |
| 3,593,809 | 7/1971 | Derry | 175/51 |
| 3,675,491 | 7/1972 | Guillet | 73/425.4 R |
| 4,227,414 | 10/1980 | Elkins | 73/425.4 R |
| 4,685,339 | 8/1987 | Philipenko | 73/864.45 |
| 4,718,289 | 1/1988 | Barrett | 73/863.57 |
| 5,033,781 | 7/1991 | Flood | 15/257.6 |
| 5,156,427 | 10/1992 | Longrie et al. | 15/257.6 |
| 5,320,393 | 6/1994 | Cortinas | 15/257.6 |
| 5,372,037 | 12/1994 | Butt | 73/153 |
| 5,413,004 | 5/1995 | Johnson, Jr. et al. | 73/863.41 |
| 5,435,399 | 7/1995 | Peterson et al. | 175/20 |

FOREIGN PATENT DOCUMENTS

| | | | |
|---|---|---|---|
| 648527 | 12/1928 | France | 15/257.4 |
| 365188 | 12/1962 | Switzerland | 15/257.2 |

*Primary Examiner*—Robert Raevis
*Attorney, Agent, or Firm*—Whyte Hirschboeck Dudek SC

[57] ABSTRACT

The present invention involves a sampler designed to collect drill cuttings which are produced during drilling of a blast hole in open-pit mining operations. The present invention is designed to capture a theoretically accurate sample which will be assayed for the gold and silver it contains (and may be appropriate for other minerals as well). The present invention obtains a larger, more representative sample and has the ability to split the sample automatically to a reasonable lab delivery weight. The design of the invention provides for sampling through the drill deck of drill machines which are commonly used in open-pit mining operations. The design of the invention allows for sampling over the entire particle trajectory and is unaffected by changes in drilling equipment. The sampler comprises a pan which is tapered and receives drill cuttings produced from drilling a blast hole. The sampler may also comprise a rear arm which is pivotally connected near the back wall of the pan, and a front arm which is pivotally connected to the pan at a location farther from the back wall of the pan relative to the rear arm.

33 Claims, 5 Drawing Sheets

U.S. Patent    Apr. 13, 1999    Sheet 1 of 5    5,894,096
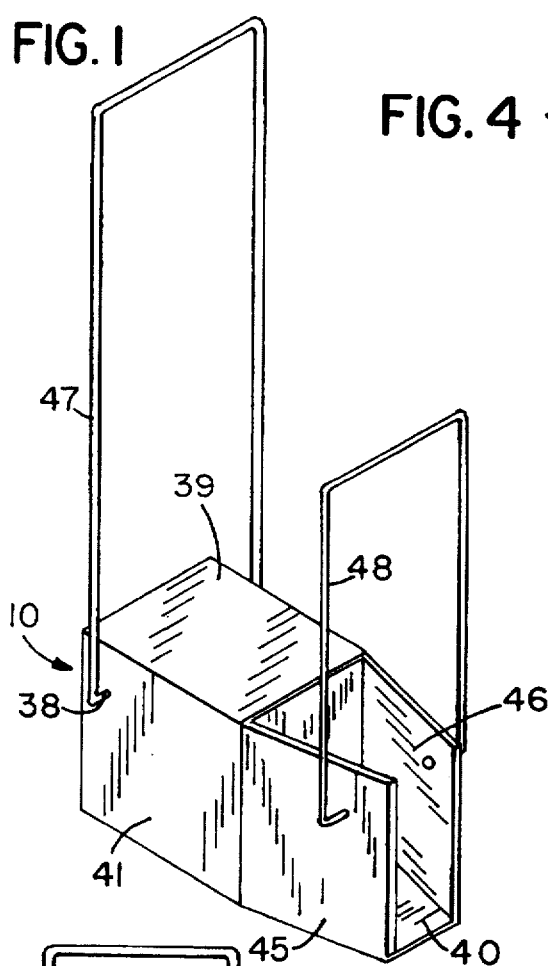
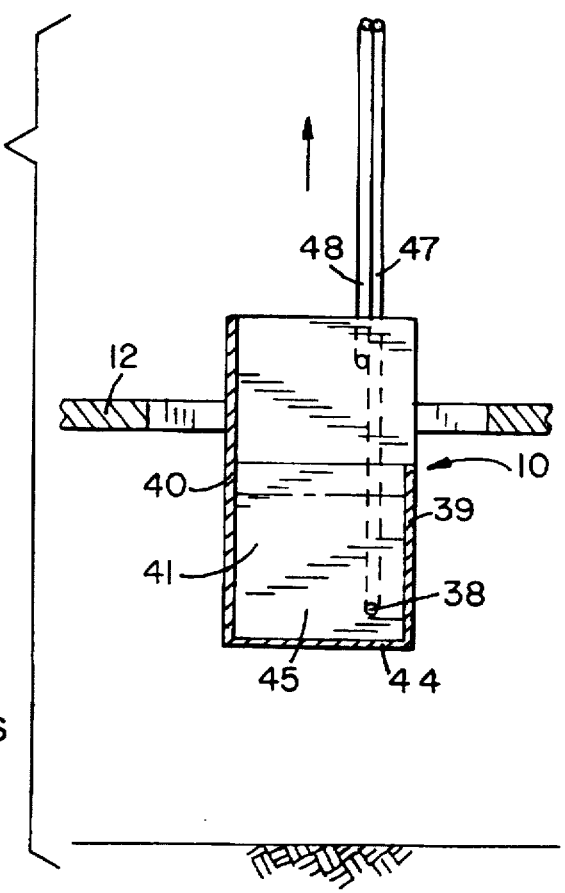
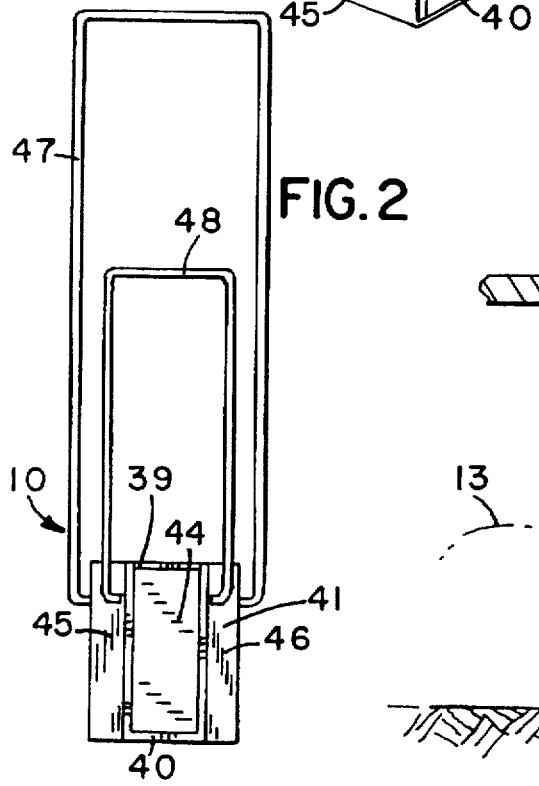
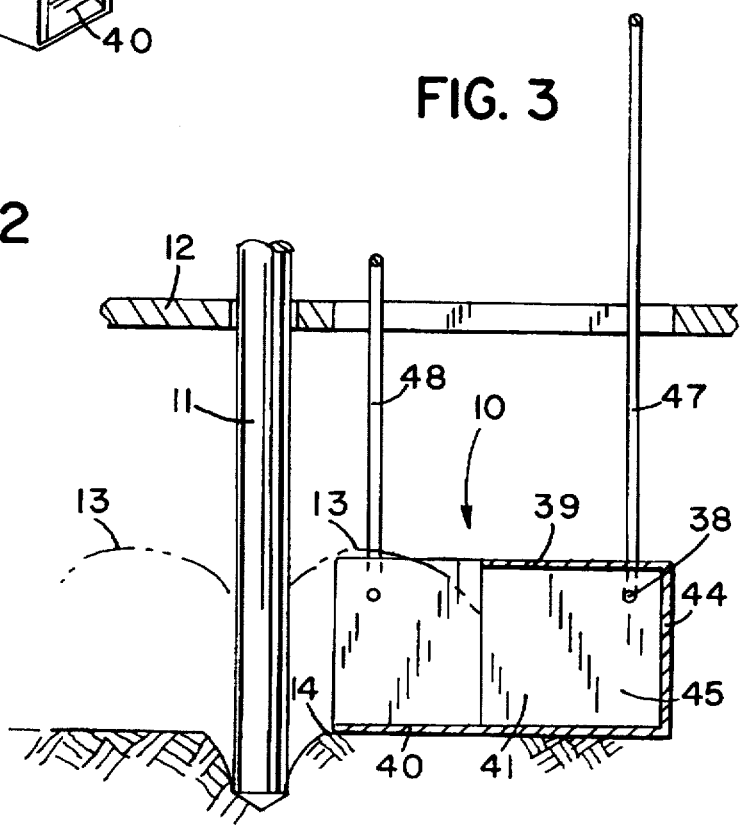

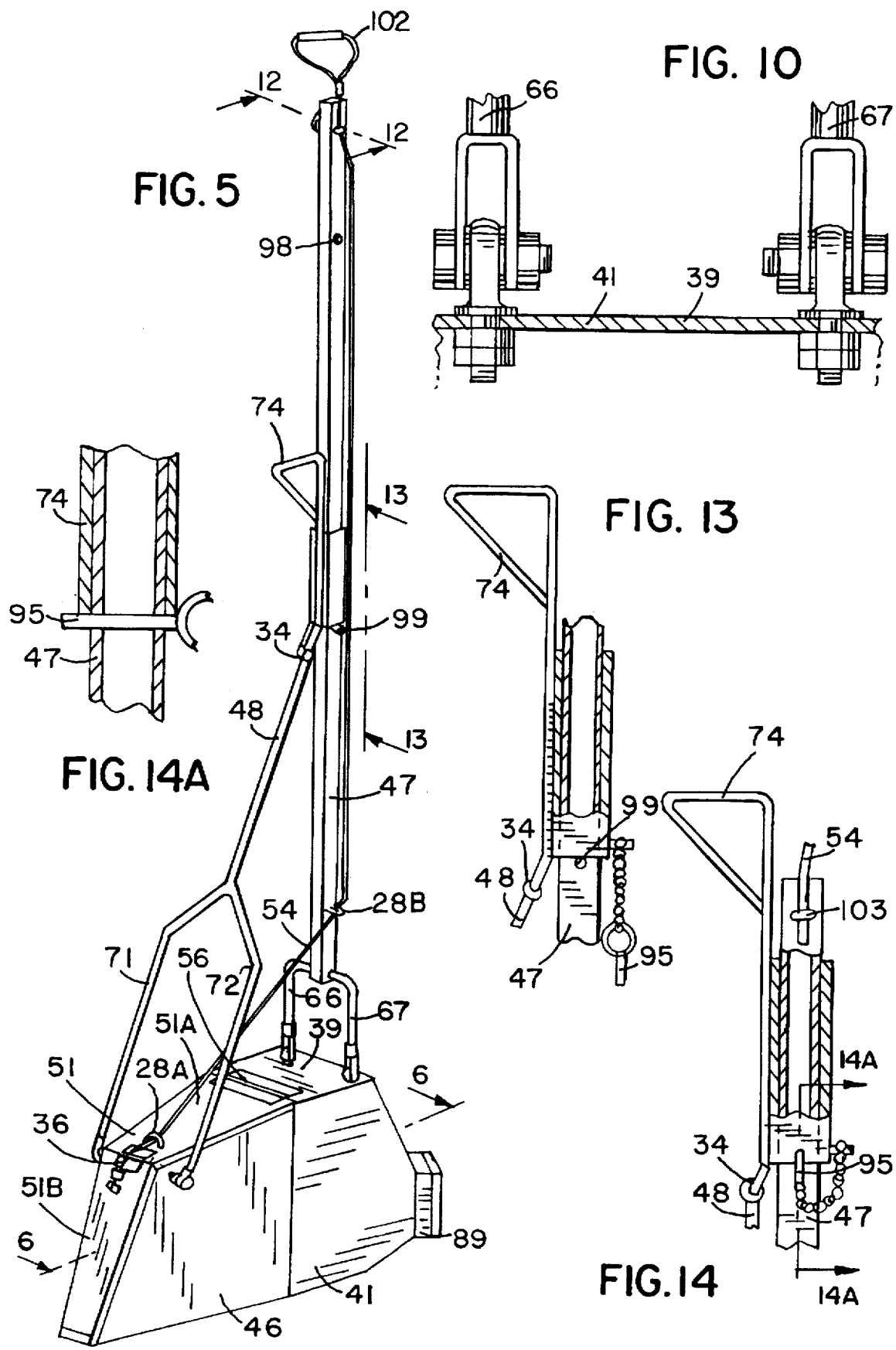

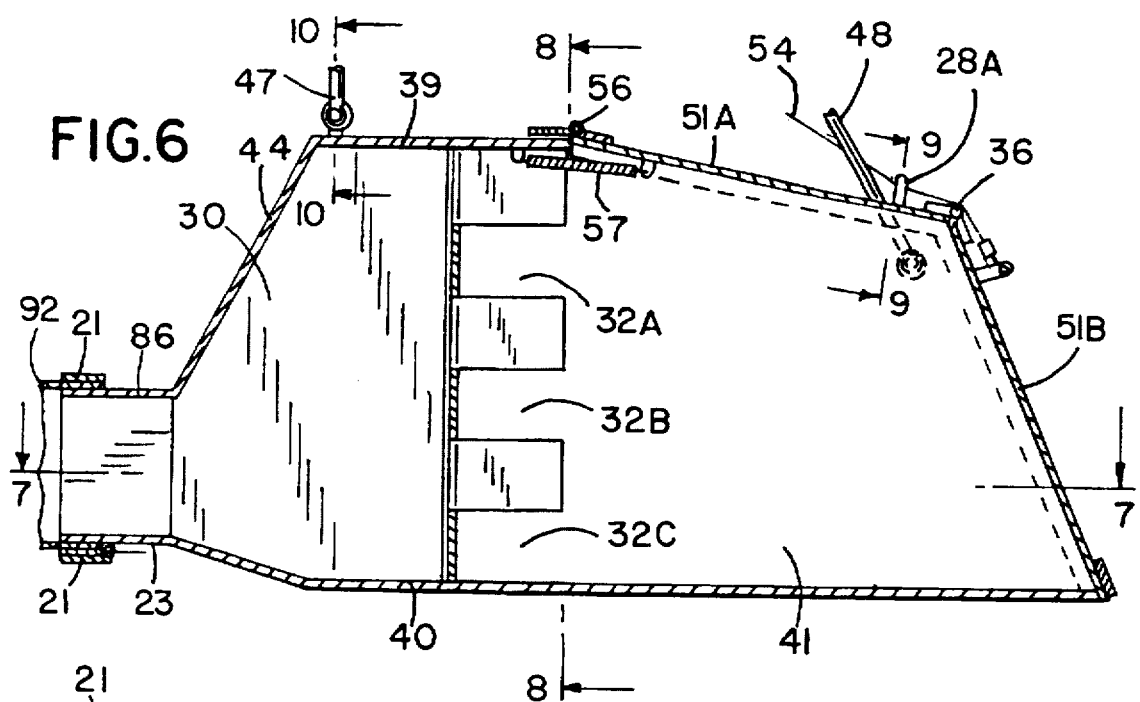
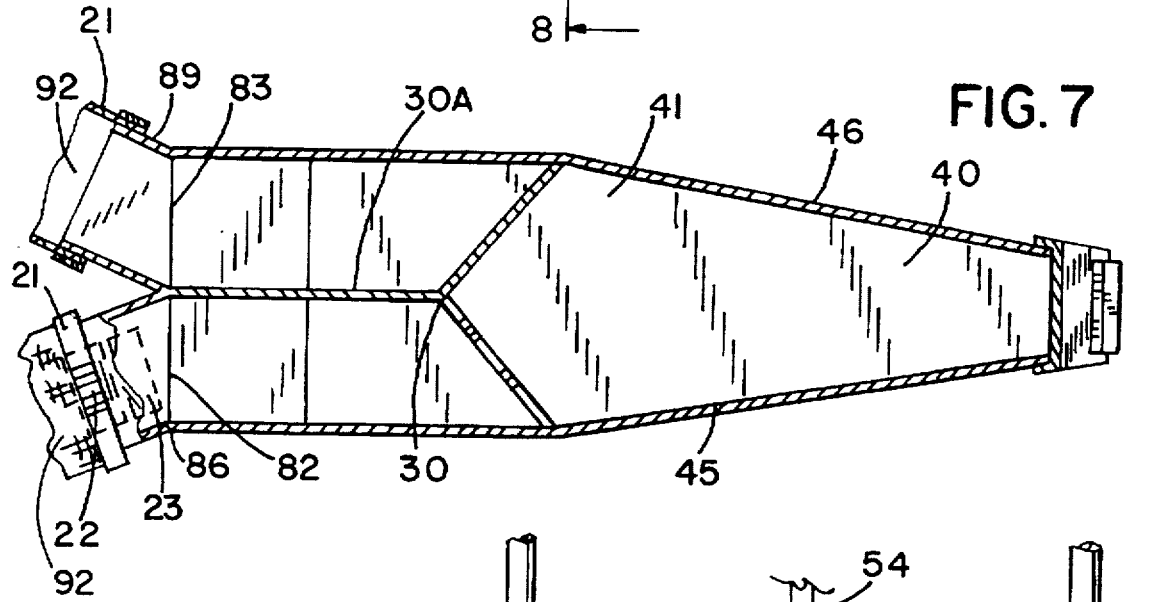
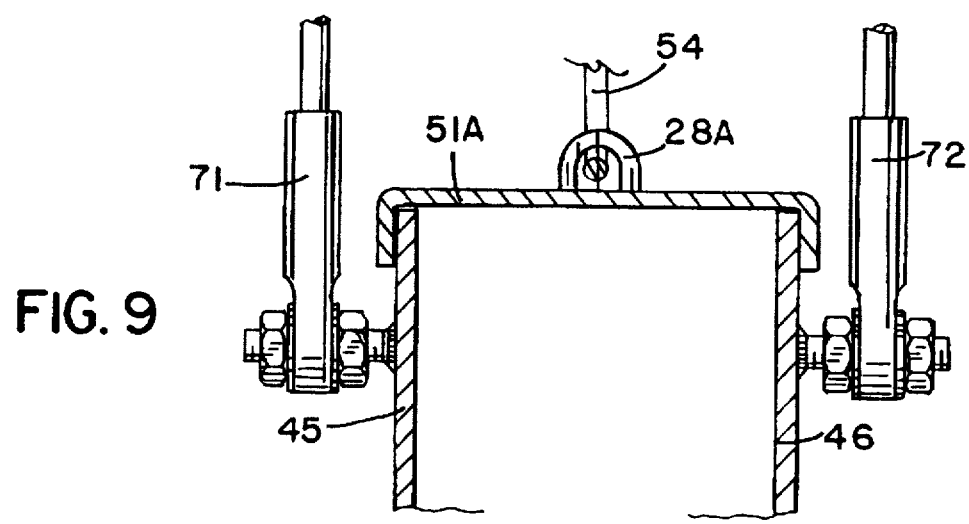

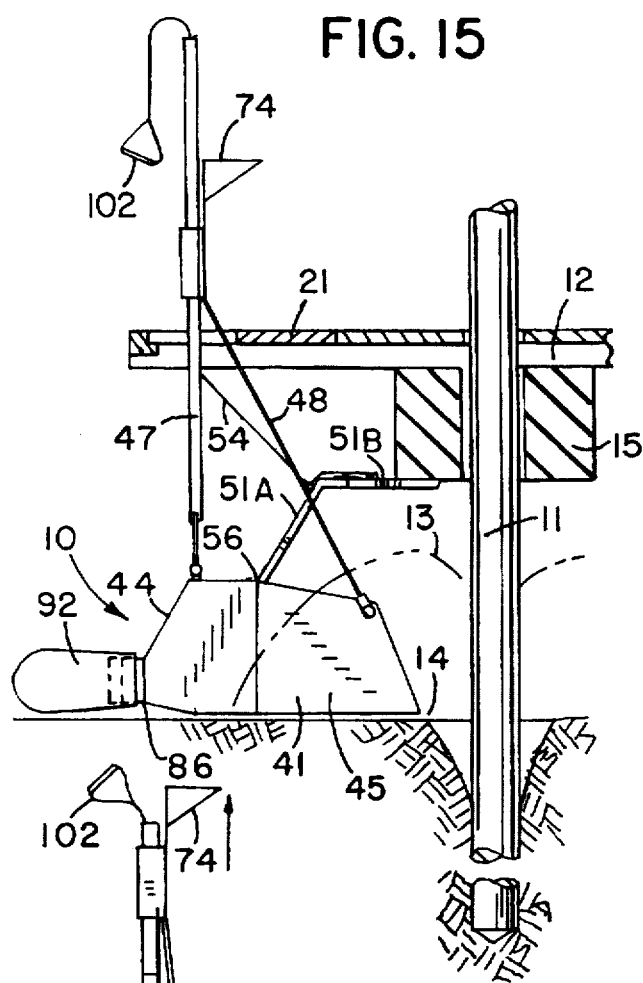
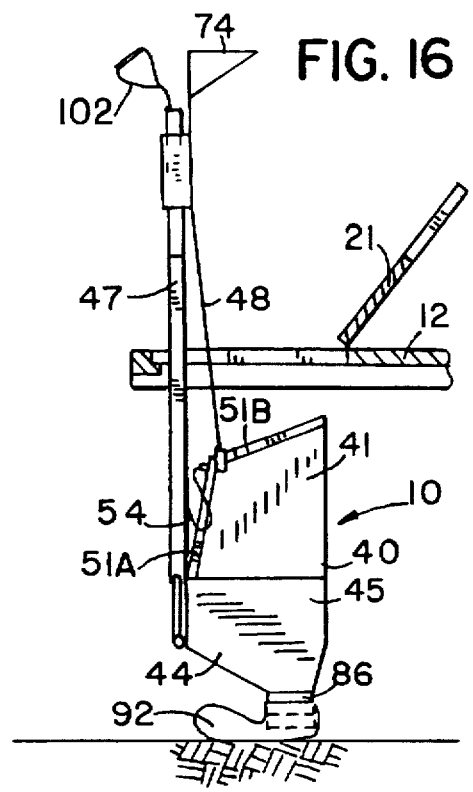
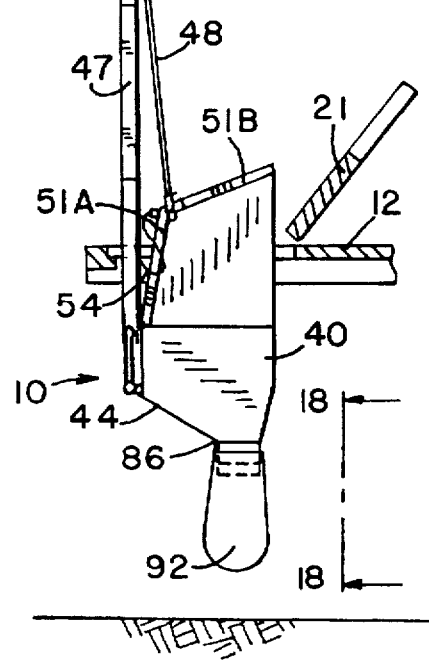
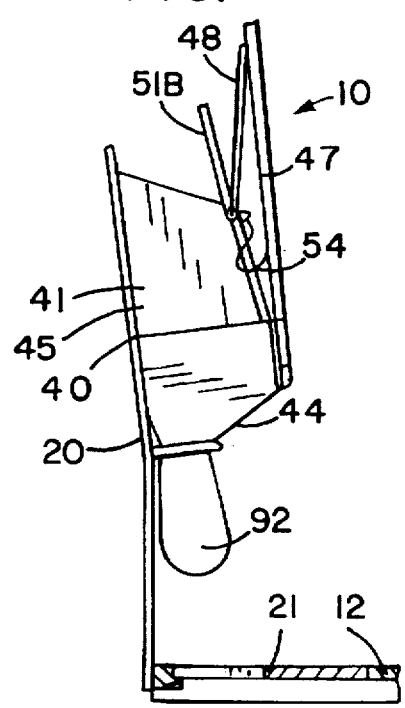

THROUGH-THE-DECK BLAST-HOLE SAMPLER

BACKGROUND OF THE INVENTION

The present invention relates to a sampler for collecting drill cuttings, and more particularly to a sampler which collects a theoretically accurate sample of drill cuttings created when blast holes are drilled in open-pit mining operations, e.g. gold or silver mining operations.

In open-pit mineral mining, blast holes are drilled and then partially filled with explosives. The explosives are detonated to turn solid rock into loose rock which can be removed from the pit for further processing in order to extract the mineral of value, e.g. gold and/or silver. The blast holes are conventionally located in a square pattern, or equilateral triangle configuration, and drilled to a uniform depth, e.g., 28 feet. The blast holes are typically half-filled with explosives. Only the top 25 feet of loose rock is removed after blasting to form a 25 foot "bench". A layer of loose rock is left in the pit to ensure that the equipment used to remove the loose rock does not come into contact with solid rock causing excessive wear and tear to the equipment. This process of drilling, blasting and removing loose rock may be repeated a number of times. Open-pit mines are often many "benches" deep.

When blast holes are drilled, samples of the drill cuttings are collected and analyzed in conjunction with samples from other drill holes in the blast hole pattern in order to determine a preferred approach for economically exploiting the mineral of interest.

Drilling is performed using large drilling machines operated by one individual in order to drill a single hole. The drill operator stands on the "deck" of the drill machine which is a platform located above the drill hole. The drill hammer and steel extend down through the drill deck into solid rock such that the cuttings which are removed from the hole during drilling remain below the drill deck. The drill deck is often surrounded by a flexible skirt in order to keep the dust and cuttings which are generated as a result of the drilling away from the operator and below the deck. As the drill hammer and steel are inserted through the drill deck, a dust rubber mounted below the drill deck provides a tight seal against the outer surface of the drill steel preventing cuttings which adhere to the drill steel from being ejected vertically through the deck.

Conventional samplers operate "through-the-deck" or "under the deck". Under the deck samplers require the drill operator to move from the drill deck to the ground in order to insert the sampler under the deck into the sampling environment, or to have a second operator who is responsible for moving the sampler into and out of the sampling environment. A through-the-deck sampler operates more efficiently because a single operator can operate the drill, and get the sampler in and out of the sampling environment, from a location above the deck.

A through-the-deck sampler is inserted into the sampling environment through an opening in the drill deck in order to obtain the sample. One conventional "through-the-deck" sampler utilizes a sample bag which is placed into a stationary tube and then mounted within a sampling rack. The sampling rack fits through an opening in the deck such that when the sampling rack is placed in the sampling environment no drill cuttings or dust can escape up through the opening. An identical sampler is often inserted through a second opening in the deck which is located on the opposite side of the drill in relation to the first opening. This second sampler is added in order to increase the volume of sample collected. The ability of this type of sampler to collect a representative sample during drilling is dramatically effected by changes in drilling equipment (i.e., hammers, air volume, etc.). These types of samplers can collect a sample for analysis, but the integrity of the sample taken can be compromised.

While known samplers are capable of sampling drill cuttings under various conditions, a need remains for a sampler which is capable of obtaining a theoretically accurate sample of blast hole drill cuttings. In addition, the need exists for a through-the-deck sampler which is portable and capable of reducing or preventing contamination of the sample during drilling. The sampler should also be capable of sampling the entire portion of cuttings ejected in its direction, and it should be able to automatically split the sample retrieved in half to provide a smaller, but representative, sample size to reduce handling costs while preserving accuracy. Finally, the need exists for a sampler which is not dependent upon any power source in order to function properly, yet still allows the sampler to close completely in order to prevent sampling during certain periods of drilling.

SUMMARY OF THE INVENTION

The present invention provides a sampler suitable for quantitatively evaluating the nature of mineral deposits located in rock formations when drilling blast holes in open-pit mining operations (particularly gold and/or silver). Specifically, the sampler is a portable, through-the-deck sampler which provides a theoretically accurate sample in order to assay for gold and/or silver (though it may be appropriate for other economic minerals as well).

The sampler comprises a pan having a back wall which is connected to a bottom wall, top wall and a pair of side walls. The side walls of the pan taper together as they extend from the back wall. The top wall does not extend as far from the back wall as the bottom wall leaving the pan open in order to receive the drill cuttings projected in its direction which are produced as a result of drilling a blast hole. The sampler also comprises a means for rotating the sampler back and forth between a substantially vertical orientation for insertion thru the drill deck, and a substantially horizontal orientation for collection of the sample below the deck. The means for rotating the sampler is preferably a rear arm pivotally connected near the back wall of the pan, and a front arm pivotally connected to the pan at a location farther from the back wall relative to the rear arm.

The present invention is designed to collect theoretically accurate samples of drill cuttings which are created from drills conventionally used at open-pit mines to drill blast holes.

BRIEF DESCRIPTION OF THE DRAWING

FIG. 1 is a perspective view of a through-the-deck blast hole sampler in a substantially horizontal orientation.

FIG. 2 is a front view of the sampler of FIG. 1 in a substantially horizontal orientation.

FIG. 3 is an environmental side elevation view of the sampler of FIG. 1 shown in a substantially horizontal orientation.

FIG. 4 is an environmental side elevation view of the sampler of FIG. 1 being pulled through-the-deck in a substantially vertical orientation.

FIG. 5 is a perspective view of a preferred embodiment of a through-the-deck blast hole sampler in a substantially horizontal orientation.

FIG. 6 is a section view of the sampler of FIG. 5 along line 6—6.

FIG. 7 is a section view of the sampler of FIG. 6 along line 7—7.

FIG. 9 is a section view of the sampler of FIG. 6 along line 9—9.

FIG. 10 is a section view of the sampler of FIG. 6 along line 10—10.

FIG. 13 is a partial section view of the sampler of FIG. 5 along line 13—13 with the sampler in a substantially horizontal orientation.

FIG. 14 is a section view of the sampler of FIG. 5 similar to the view in FIG. 13 except that the handle is positioned along the rear arm with the sampler in a substantially vertical orientation.

FIG. 14A is a section view of the sampler of FIG. 14 along line 14A—14A.

FIG. 15 is an environmental side elevation view of the sampler of FIG. 5 in a substantially horizontal orientation with the cover open ready for sampling.

FIG. 16 is an environmental side elevation view of the sampler of FIG. 5 in a substantially vertical orientation below the deck.

FIG. 17 is an environmental side elevation view of the sampler of FIG. 5 in a substantially vertical orientation being pulled up through the deck.

FIG. 19 is an environmental side elevation view of the sampler of FIG. 5 hanging in a rack with the sample collected in the attached sample bag.

DETAILED DESCRIPTION OF INVENTION

Figure 8:
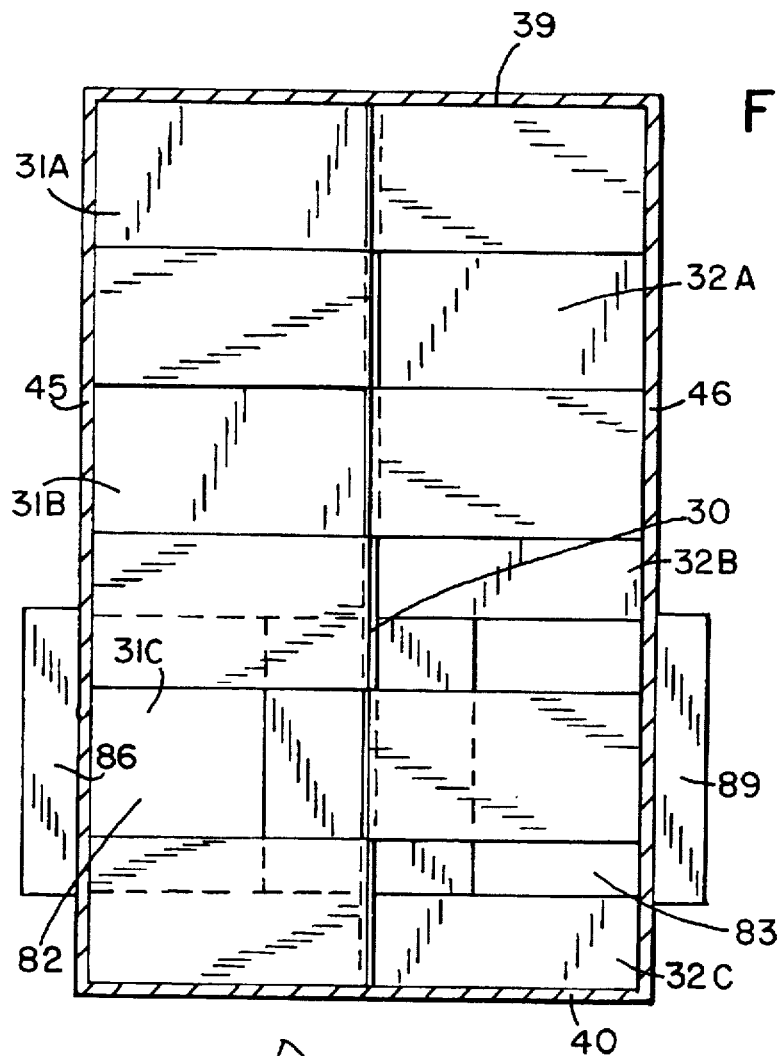
FIG. 8 is a section view of the sampler of FIG. 6 along line 8—8.

Similar reference characters denote corresponding features consistently throughout the attached drawings. Various items of equipment such as fasteners, fittings, etc., are omitted so as to simplify the description. However, those skilled in the art will realize that such conventional equipment can be employed as desired.

As shown in FIGS. 1–4, the present invention is a blast hole sampler 10 which comprises pan 41 and a means for rotating the sampler back and forth between a substantially vertical orientation and a substantially horizontal orientation, preferably front arm 48 and rear arm 47. Pan 41 is preferably designed to obtain a theoretically accurate sample of drill cuttings created when blast holes are drilled in open-pit mining operations according to sampling theory such as that described by Francis F. Pitard in *Pierre Gy's Sampling Theory and Sampling Practice* (2d ed.). First side wall 45, second side wall 46, top wall 39 and bottom wall 40 of pan 41 extend from back wall 44. First side wall 45 and second side wall 46 taper together as they extend from back wall 44.

Rear arm 47 is pivotally connected to pan 41 near back wall 44, while front arm 48 is pivotally connected to pan 41 farther from back wall 44 relative to rear arm 47.

Blast-hole sampler 10 is shown in a substantially horizontal orientation ready for sampling in FIG. 3. Drill 11 extends through drill deck 12 into the ground and rotates during operation generating cuttings 13.

Sampling begins with a drill operator placing sampler 10 through deck 12 while sampler 10 is in a substantially vertical orientation as shown in FIG. 4. Once pan 41 is completely through deck 12, front arm 48 is lowered such that pan 41 rotates into a substantially horizontal orientation about pivot joint 38. Sampler 10 is then placed on the ground relative to drill 11 such that when drill 11 is in operation a theoretically accurate sample of the cuttings 13 is projected into pan 41. Pan 41 is preferably placed at the edge of collared hole 14. Once drilling is completed, sampler 10 is lifted and front arm 48 is raised such that pan 41 rotates back into a substantially vertical orientation and pulled back through deck 12. The collected sample is removed from pan 41 and sent for analysis.

Pan 41 is preferably designed in order to collect sample over the entire drill cutting trajectory range without any overflow prior to completion of sampling in the desired drilling interval. In addition, sampler 10 is preferably designed such that it is unaffected when used with a variety of drilling equipment (i.e., different drill hammers, drill bits, varying air pressures, etc.).

Deck 12 conventionally has a door 21, which is in the closed position when sampler 10 is sampling, as shown in FIG. 15. When door 21 is closed there is minimum exposure of the work environment above the deck to the dust generated during drilling below the deck. Door 21 is opened when the operator removes sampler 10 from below the deck as shown in FIGS. 16 and 17.

In another embodiment, sampler 10 includes cover 51, which is attached to pan 41 near back wall 44, as shown in FIGS. 5, 6, 15, 16, 17 and 19. Cover 51 may be attached to pan 41 using a variety of conventional fasteners, preferably hinge 56. Cover 51 may also be attached directly to back wall 44 such that there is no top wall 39.

Cover 51 preferably maintains a moderately tight seal in the closed position in order to prevent sample loss and/or contamination during rotation of pan 41 into the extraction position as well as subsequent extraction through deck 12. Spring 57 may be attached to cover 51 and pan 41 in order to bias cover 51 in the closed position as shown in FIG. 6.

Sampling drill cuttings which are generated at the beginning of drilling a blast hole is usually not desired, and conventional drilling equipment usually generates excessive air pressure under the skirt when starting to drill, i.e. collar, a hole. Cover 51 is preferably weighted in order to prevent cover 51 from opening when sampler 10 is exposed to excessive air pressure during collaring of the blast hole.

One preferred design for cover 51 as shown in FIGS. 5 and 6 has rear section 51A attached to pan 41 near back wall 44, while front section 51B is attached to rear section 51A. Front section 51B is attached to rear section 51A by any conventional fastening means, preferably with hinge 36.

Front section 51B can be moved in order to expose the interior of pan 41 and allow the operator to clean the interior of pan 41 between sampling operations as shown in FIG. 19. Cleaning of pan 41 may be done using a variety of techniques known in the art, preferably, by exposing the interior of the pan to a stream of air traveling at high velocity.

Figure 12:
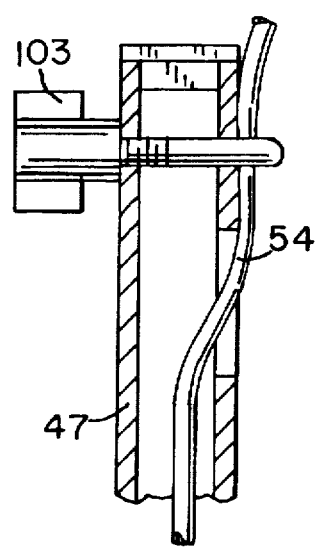
FIG. 12 is a section view of the sampler of FIG. 5 along line 12—12.

Cover 51 is preferably opened and closed by use of cable 54. Cable 54 is attached to cover 51, preferably front section 51B. Cable 54 preferably extends up through links 28A and 28B paralleling rear arm 47 ending in loop 102, and is preferably clamped to rear arm 47 using clamp 103 as shown in FIGS. 5 and 12. Loop 102 remains above deck 12 when sampler 10 is below deck 12 in the sampling position providing an easy gripping point for an operator standing on deck 12 to raise and lower cover 51 using cable 54 as shown in FIG. 15. Sampling may not be desired during the entire drilling operation. The ability of the drill operator to open and close cover 51 from a location above deck 12 allows for sampling to be done at the driller's discretion. Blast holes are conventionally drilled to a desired depth, e.g. 28 feet, and sampling is preferably not done when drilling begins, i.e. when the hole is being collared, and during the last few feet of drilling because sampling is conventionally done only to the depth of the desired bench height.

Cover 51 is preferably designed such that when sampler 10 is below deck 12 ready for sampling, and cover 51 is open, cover 51 is in contact with dust rubber 15 and provides protection against contaminants falling into pan 41 as shown in FIG. 15. Potential contaminants include materials which have adhered to the underside of deck 12, such contaminants often come loose as a result of vibration in deck 12 during drilling, and may fall into pan 41 unless cover 51 is oriented above pan 41 during sampling. Cover 51 also preferably deflects drill cutting whose trajectory would normally be over pan 41 into pan 41 for collection as part of the sample.

Sampler 10 can be mounted on rack 20 by varying means, e.g., hooks or bungee cords, in order to remove sample collector 92, as shown in FIG. 19, or for storage when sampler 10 is not in use.

As shown in FIGS. 5 and 10 rear arm 47 preferably comprises first support 66 and second support 67. First support 66 is pivotally connected to pan 41 near back wall 44 and near first side wall 45, while second support 67 is pivotally connected to pan 41 near back wall 44 and near second side wall 46.

As shown in FIGS. 5, 9 and 15, front arm 48 preferably comprises first support 71 and second support 72. First support 71 is pivotally connected to pan 41 near first side wall 45, while second support 72 is pivotally connected to pan 41 near second side wall 46. Both first support 71 and second support 72 are connected to pan 41 at a location farther from back wall 44 relative to rear arm 47. First support 71 and second support 72 are preferably spaced far enough apart such that cover 51 can open and close without interference from either support.

As shown in FIGS. 5, 13, 14 and 14A, front arm 48 preferably has a handle, more preferably an angular handle 74 capable of pivoting about joint 34, and sliding up and down about rear arm 47. Handle 74 remains above deck 12 when sampler 10 is in position for sampling, which allows a drill operator standing on deck 12, to lift front arm 48 and rotate pan 41 into a substantially vertical orientation so sampler 10 may be lifted up through deck 12 as shown in FIGS. 16 and 17. Handle 74 preferably slides up and down about rear arm 47 to place sampler 10 in the appropriate position for sampling or extraction.

Handle 74 preferably has means for securing pan 41 in a substantially horizontal orientation and a substantially vertical orientation. Upper pin opening 98 is located on rear arm 47 such that when pan 41 is in a substantially vertical orientation, pin 95 can be secured in upper pin opening 98. Lower pin 99 is fixed on rear arm 47 such that when pan 41 is lowered into a substantially horizontal orientation (for sampling) lower pin 99 acts as a stopper maintaining the sampler in a substantially horizontal orientation.

Back wall 44 may have one or more openings, e.g. 1 or 2, which allow the sample collected during drilling to move from pan 41 as sampler 10 is rotated from a substantially horizontal orientation into a substantially vertical orientation and lifted through deck 12.

Figure 11:
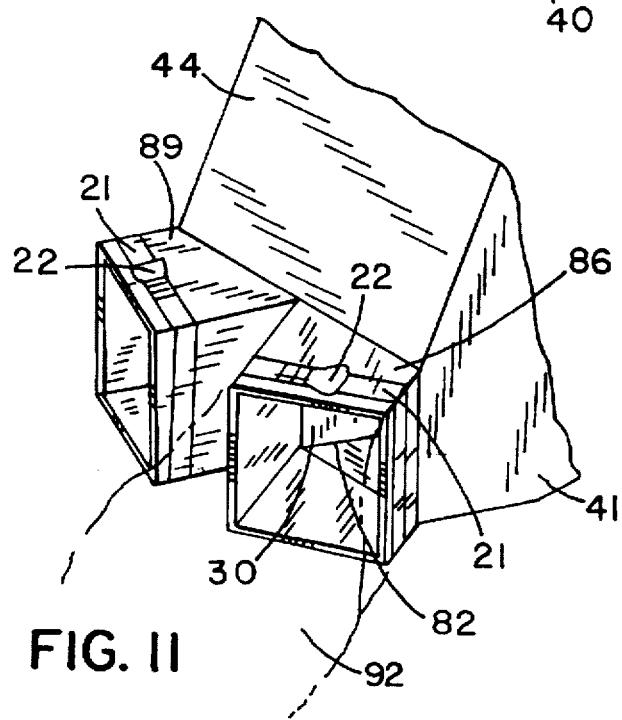
FIG. 11 is a partial perspective view of the rear of the sampler of FIG. 5.
Figure 18:
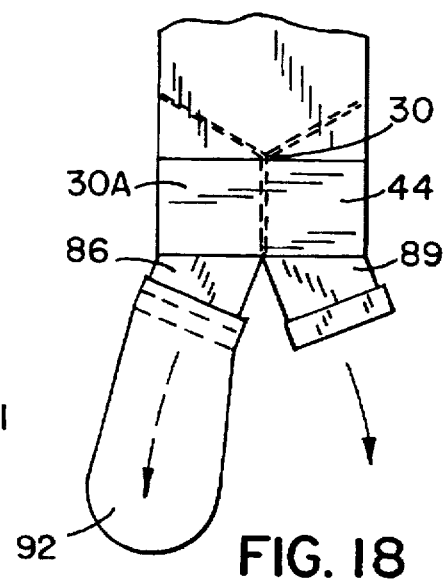
FIG. 18 is a partial view of the sampler of FIG. 17 viewed from line 18—18.

As shown in FIGS. 7, 11 and 18, sampler 10 preferably has first conduit 86 connected to back wall 44 about first opening 82, and more preferably has second conduit 89 connected to back wall 44 about second opening 83.

Sample collector 92 may be attached to either first conduit 86 or second conduit 89 in order to collect a portion of the sample (typically half) which is received from pan 41. In addition, a second sample collector may be attached to the other conduit such that all the sample within pan 41 is collected. Preferably, the sample collectors are a type of bag, e.g. a sealable cloth bag, which is capable of collecting sample and maintaining the integrity of the sample during delivery to a different location for analysis.

As shown in FIGS. 6, 7 and 11, the preferred means for mounting sample collector 92 is band 21 which is preferably attached to hinge 23. One side of hinge 23 is fastened to the bottom of first conduit 86 and/or second conduit 89 while the other half of hinge 23 is attached to band 21. Hinge 23 can swing out of the way allowing insertion and removal of sample collectors from either first conduit 86 or second conduit 89. Band 21 attaches sample collector 92 about either first conduit 86 or second conduit 89 and is preferably attached using clamp 22.

The interior of pan 41 preferably includes a splitter capable of accurately splitting the sample collected during drilling such that one half of the sample falls from pan 41 through first opening 82 and the other half of the sample from pan 41 through second opening 83. Splitting the sample before it leaves pan 41 can be done using any splitter which accurately splits the sample collected in half.

As shown in FIGS. 6, 7, 8, 11 and 18, splitter 30 preferably has dividing wall 30A extending into pan 41 from back wall 44 between first opening 82 and second opening 83. Preferably, dividing wall 30A symmetrically divides the volume of pan 41 in half near back wall 44, and more preferably continues to extend into pan 41 connecting alternatingly to first side wall 45 and second side wall 46 such that the only access through pan 41 to first opening 82 and second opening 83 is through openings 31A, 31B, 31C, 32A, 32B and 32C. When pan 41 is lifted through deck 12 after sampling and rotated into a substantially vertical orientation, the sample collected in pan 41 is split. Half the sample will travel through openings 31A, 31B and 31C and then through first opening 82, and the other half of the sample will travel through openings 32A, 32B and 32C and then through second opening 83.

The ability of sampler 10 to automatically split the sampler to a reasonable delivery weight provides several advantages. First, there is significant labor savings in not having to split the sample in a separate operation. Second, there is reduced risk of injury to drill operators because the weight of the sample(s) collected and sent for analysis are reduced by one half. Finally, the time to perform the analysis of the sample is reduced because of the smaller sample size.

Although the present invention has been described in considerable detail with reference to certain preferred versions thereof, other versions are possible. The pan may contain a plurality of separate openings, and there may be variations in the design of the pan, cover, front arm, rear arm, splitter and means for lifting the cover. Many variations and modifications can be made by one skilled in the art without departing from the spirit and scope of the invention.

What is claimed is:

1. A through the deck sampler for collecting drill cuttings, the sampler adapted to be placed through a drill deck from above in a substantially vertical orientation, rotated into a substantially horizontal orientation for collecting the drill cuttings and rotated back into the substantially vertical orientation to be pulled up through the deck after the sample is collected, the sampler comprising:
  a) a pan for receiving the drill cuttings, the pan having a back wall connected to a bottom wall, a first side wall and a second side wall, the first and second side walls (i) connected to the bottom wall and (ii) tapering together as they extend from the back wall; and
  b) means for pivoting the pan between the substantially vertical orientation and the substantially horizontal orientation.

2. The sampler of claim 1 further comprising:
  a) a cover attached to pan for enclosing the pan when the cover is in a closed position; and
  b) means for maneuvering the cover into and out of the closed position from a remote location.

3. The sampler of claim 2 in which the means for maneuvering the cover is a cable attached to the cover.

4. The sampler of claim 3 further comprising means for clamping the cable to the rear arm.

5. The sampler of claim 2 further comprising a top wall connected to the back wall and the first and second side walls, the top wall does not extend as far from the back wall as the bottom wall.

6. The sampler of claim 5 in which the cover is attached to the top wall by a hinge.

7. The sampler of claim 6 in which the cover is weighted such that the cover is biased in the closed position.

8. The sampler of claim 6 further comprising a spring attached to the cover and attached to the pan for biasing the cover in the closed position.

9. The sampler of claim 5 in which the cover includes a front section and a rear section, the rear section attached to the top wall of the pan and the front section attached to the rear section.

10. The sampler of claim 2 in which the cover is attached to the back wall by a hinge.

11. The sampler of claim 10 further comprising a spring attached to the cover and attached to the pan for biasing the cover in the closed position.

12. The sampler of claim 2 in which the cover includes a front section and a rear section, the rear section attached to the back wall of the pan and the front section attached to the rear section.

13. The sampler of claim 12 in which the rear section is attached to the back wall by a hinge and the front section is attached to the rear section by a hinge.

14. The sampler of claim 13 further comprising a spring attached to the rear section and the pan for biasing the cover in the closed position.

15. The sampler of claim 1 in which the means for pivoting the pan between the substantially vertical orientation and the substantially horizontal orientation comprises:
  a) a rear arm pivotally connected to the pan; and
  b) a front arm pivotally connected to the pan at a location farther from the back wall of the pan relative to the rear arm.

16. The sampler of claim 15 in which the rear arm comprises a first support and a second support, the first support pivotally connected to the pan near the back wall and near the first side wall, and the second support pivotally connected to the pan near the back wall and near the second side wall.

17. The sampler of claim 16 in which the front arm comprises a left support and a right support, the left support of the front arm pivotally connected to the pan near the first side wall and farther from the back wall relative to the rear arm, the right support of the front arm pivotally connected to the pan near the second side wall and farther from the back wall relative to the rear arm.

18. The sampler of claim 15 in which the front arm comprises a first support and a second support, the first support of the front arm pivotally connected to the pan near the first side wall and farther from the back wall relative to the rear arm, the second support of the front arm pivotally connected to the pan near the second side wall and farther from the back wall relative to the rear arm.

19. The sampler of claim 15 in which the front arm includes a handle.

20. The sampler of claim 19 in which the handle on the front arm is slidably mounted about the rear arm.

21. The sampler of claim 1 in which the back wall has an opening and an outside surface further comprising:
  a) a conduit attached to the outside surface of the back wall about the opening in the back wall; and
  b) a sample collector attached to the conduit for receiving the drill cuttings which flow from the pan through the conduit as the sampler is rotated into the substantially vertical after sampling.

22. The sampler of claim 21 in which the sample collector is a bag.

23. The sampler of claim 22 in which the bag is attached to the conduit by a band having a clamp.

24. The sampler of claim 1 in which the back wall has a first opening, a second opening, an inside surface and an outside surface further comprising:
  a) a first conduit attached to the outside surface of the back wall about the first opening;
  b) a first sample collector attached to the first conduit; and
  c) a second conduit attached to the outside surface of the back wall about the second opening in the back wall.

25. The sampler of claim 24 further comprising a second sample collector attached to the second conduit.

26. The sampler of claim 25 in which the first sample collector and the second sample collector are bags.

27. The sampler of claim 24 in which the first sample collector is a bag and further comprising a hinge attached to the first conduit and a band removably attached to the hinge such that the band can be positioned away from the first conduit allowing the bag to be placed about the first conduit before repositioning the band around the bag in order to secure the bag around the first conduit.

28. The sampler of claim 27 in which the band includes a clamp for securing the band about the bag.

29. The sampler of claim 24 further comprising a splitter attached to the inside surface of the back wall, between the first opening and the second opening.

30. The sampler of claim 29 in which the splitter is a dividing wall extending into the pan such that the dividing wall is an equal distance from the first side wall and the second side wall.

31. The sampler of claim 30 in which the dividing wall extends further into the pan and alternatingly connects with the first side wall and the second side wall to form a plurality of left-hand openings and a plurality of right hand openings such that the only access to the first opening through the pan is through the plurality of left-hand openings, and the only access to the second opening through the pan is through the plurality of right-hand openings.

32. A through the deck sampler for collecting drill cuttings, the sampler adapted to be placed through the drill deck from above in a substantially vertical orientation, rotated into a substantially horizontal orientation for collecting the drill cuttings and rotated back into the substantially vertical orientation to be pulled up through the deck after the sample is collected, the sampler comprising:

a) a pan having a back wall connected to a bottom wall, a top wall, a first side wall and a second side wall, the first side wall and the second side wall (i) connected to the bottom wall and the top wall and (ii) tapering together as they extend from the back wall, the top wall is does not extend as far from the back wall as the bottom wall;

b) a rear arm comprising a first support and a second support, the first support pivotally connected to the pan near the back wall and near the first side wall, and the second support pivotally connected to the pan near the back wall and near the second side wall;

c) a front arm comprising a left support and a right support, the left support pivotally connected to the pan near the first side wall and farther from the back wall relative to the rear arm, the right support pivotally connected to the pan near the second side wall farther from the back wall relative to the rear arm, the front arm is raised and lowered to move the sampler between the substantially vertical orientation and the substantially horizontal orientation;

d) a cover for enclosing the pan when the cover is in a closed position having a front section and a rear section, the rear section attached by a hinge to the top wall and the front section attached by a hinge to the rear section, the front section weighs more than the rear section to bias the cover in the closed position;

e) a cable attached to the cover for maneuvering the cover into and out of the closed position;

f) means for clamping the cable to the rear arm; and g) a spring attached to the rear section and the pan for biasing the cover in the closed position.

33. A blast-hole sampler comprising:

a) a pan having a back wall connected to a bottom wall, a top wall, a first side wall and a second side wall, the first side wall and the second side wall (i) connect to the bottom wall and the top wall and (ii) taper together as they extend from the back wall, the top wall does not extend as far from the back wall as the bottom wall, the back wall having a first opening, a second opening, an inside surface and an outside surface;

b) a rear arm comprising a first support and a second support, the first support pivotally connected to the pan near the back wall and near the first side wall and the second support pivotally connected to the pan near the back wall and near the second side wall;

c) a front arm comprising a left support and a right support, the left support pivotally connected to the pan near the first side wall and farther from the back wall relative to the rear arm, the right support pivotally connected to the pan near the second side wall and farther from the back wall relative to the rear arm, the front arm is raised and lowered to move the sampler between the substantially vertical orientation and the substantially horizontal orientation;

d) a cover for enclosing the pan when the cover is a closed position having a front section and a rear section, the rear section attached by a hinge to the top wall and the front section attached by a hinge to the rear section, the front section weighs more than the rear section to bias the cover in the closed position;

e) a cable attached to the cover for maneuvering the cover into and out of the closed position;

f) means for clamping the cable to the rear arm; and g) a spring attached to the cover and the pan for biasing the cover into the closed position;

h) a first conduit attached to the outside surface of the back wall about the first opening;

i) a first sample collector attached to the first conduit;

j) a second conduit attached to the outside surface of the back wall about the second opening;

k) a splitter attached to the inside surface of the back wall.

* * * * *